United States Patent
Donnelly et al.

[11] Patent Number: 5,569,733
[45] Date of Patent: Oct. 29, 1996

[54] TERTIARY AMINOUREA COMPOSITIONS AND THEIR USE AS CATALYSTS IN CURABLE COMPOSITIONS

[75] Inventors: Karen D. Donnelly, Allison Park; Joseph M. Makhlouf, Mars, both of Pa.

[73] Assignee: PPG Industries, Inc., Pittsburgh, Pa.

[21] Appl. No.: 220,659

[22] Filed: Mar. 31, 1994

[51] Int. Cl.$^6$ ............................................. C08G 18/32
[52] U.S. Cl. ....................... 528/61; 528/103; 528/211; 528/905; 502/200; 502/511; 525/423; 428/423.1; 427/372.2
[58] Field of Search .................. 528/45, 103, 211, 528/905, 61; 427/372.2; 428/423.1; 525/423; 502/200, 511

[56] References Cited

U.S. PATENT DOCUMENTS

| | | | |
|---|---|---|---|
| 4,183,883 | 1/1980 | Blair | 264/40.1 |
| 4,409,381 | 10/1983 | Holubka | 528/45 |
| 4,578,424 | 3/1986 | Goel | 525/109 |
| 4,711,934 | 12/1987 | Paar et al. | 525/452 |
| 4,851,486 | 7/1989 | Paar | 525/528 |
| 4,940,768 | 7/1990 | Honel et al. | 528/45 |
| 5,096,555 | 3/1992 | Schupp et al. | 204/181.7 |
| 5,098,966 | 3/1992 | Scholten et al. | 525/533 |
| 5,218,063 | 6/1993 | Kimball | 525/531 |
| 5,225,461 | 7/1993 | Kamikado et al. | 525/528 |

FOREIGN PATENT DOCUMENTS

| | | |
|---|---|---|
| 0 452 866 A3 | 10/1991 | European Pat. Off. . |
| 3027796 | 2/1982 | Germany . |

*Primary Examiner*—Nathan M. Nutter
*Assistant Examiner*—Duc Truong
*Attorney, Agent, or Firm*—Krisanne Shideler; Kenneth J. Stachel

[57] ABSTRACT

A composition which is the reaction product of (i) a material having the structure

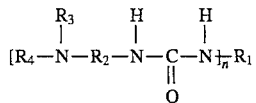

where $R_1$ is an organic radical having 6 to 25 carbon atoms; $R_2$ is alkylene having 1 to 4 carbon atoms; $R_3$ and $R_4$ are independently alkyl having 1 to 4 carbon atoms and n is 2–4 and (ii) an acidic hydrogen-containing compound. The compositions are useful as catalyst in induction curable adhesive compositions.

36 Claims, No Drawings

TERTIARY AMINOUREA COMPOSITIONS AND THEIR USE AS CATALYSTS IN CURABLE COMPOSITIONS

FIELD OF THE INVENTION

The present invention relates to compositions useful as catalysts in curable compositions, particularly induction-cured epoxy adhesives. The invention also relates to the curable compositions containing these compositions.

BACKGROUND OF THE INVENTION

Induction cure of adhesives is used in situations where an adhesive is applied to an area which is difficult to heat by conventional oven baking techniques. In automobiles and trucks such an area is a flanged fixture such as a reinforcing plate for an automotive body panel. An induction coil operating with a high electrical frequency is brought into close proximity to the flanged fixture. The instantaneous heating effect raises the metal surface temperature to 150° C. or above to initiate cure of the adhesive. Cure time can vary from about 4 to 45 seconds, depending on the heat generated and the cure rate of the adhesive used.

Induction cure is viewed as a viable option to spot welding because metal finishing is minimal and soundness of the bonded fixture virtually eliminates corrosion, squeaks, and rattles associated with spot welds.

Major drawbacks to induction-cured adhesives of the prior art include poor long term stability due to catalysts which are too reactive, variability in performance, and the high cost of both adhesives and suitable catalysts.

There is a need, therefore, to develop a catalyst and a curable composition containing such a catalyst with a suitable degree of reactivity for use in an induction cure adhesive which overcomes the drawbacks of the prior art.

SUMMARY OF THE INVENTION

In accordance with the present invention, there is provided a composition which is the reaction product of:
(i) a material having the structure:

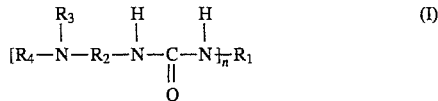

wherein $R_1$ is an organic radical having 6 to 25 carbon atoms, $R_2$ is alkylene having one to four carbon atoms; $R_3$ and $R_4$ are independently alkyl having one to four carbon atoms; and n is 2–4; and (ii) an acidic hydrogen-containing compound.

Also provided is a curable composition comprising (a) a polyepoxide resin, (b) a crosslinking agent, (c) an accelerator, and (d) the composition described above, and a process for induction curing of the curable composition.

DETAILED DESCRIPTION

The material of I is preferably an oligomer wherein $R_1$ is a divalent, trivalent or tetravalent organic radical preferably divalent and can be aliphatic such as hexamethylene, cycloaliphatic or substituted cycloaliphatic such as cyclohexylene and 1,1,3,3-tetramethylcyclohexylene, or aromatic such as phenylene. $R_1$ preferably is substituted cycloaliphatic, particularly 1,1,3,3-tetramethylcyclohexylene. Examples of $R_2$ include ethylene, n-propylene, and iso- and n-butylene. $R_3$ and $R_4$ are both preferably methyl groups.

The material of (i) can be prepared by reacting an organic polyisocyanate with a diamine containing a primary or secondary amine group and a tertiary amine group. Suitable polyisocyanates include aliphatic, cycloaliphatic, or aromatic polyisocyanates. Diisocyanates are preferred, although higher polyisocyanates can be used. Examples of suitable aromatic diisocyanates are 4,4'-diphenylmethane diisocyanate, 1,3-bis(1-isocyanato- 1-methylethyl)benzene and derivatives thereof, and toluene diisocyanate. Examples of suitable aliphatic diisocyanates are straight chain aliphatic diisocyanates such as 1,6-hexamethylene diisocyanate and cycloaliphatic diisocyanates including isophorone diisocyanate and 4,4'-methylene-bis(cyclohexyl isocyanate). Examples of suitable higher polyisocyanates are 1,2,4-benzene triisocyanate, polymethylene polyphenyl isocyanate and the isocyanurate of isophorone diisocyanate. Isophorone diisocyanate is preferred.

Examples of diamines containing a primary or secondary amine group and a tertiary amine group are dimethylaminopropylamine and dimethylaminoethylamine. Dimethylaminopropylamine is preferred.

The diamine and polyisocyanate are combined in an equivalent ratio of about 1:1. The diamine is heated to about 50° C., and the polyisocyanate is added over a period of time in the range of about one to two hours, preferably about two hours. The temperature of the reaction mixture generally increases and is held at an elevated temperature, preferably 130° to 170° C., until the polyisocyanate is completely reacted.

The acidic hydrogen-containing compound of (ii) is preferably a solid compound, more preferably crystalline, so that the reaction product of (i) and (ii) has a high melting point. When the reaction product is used as a catalyst in a curable composition, the high melting point prevents any curing from taking place before the application of heat. This improves the long term stability of curable compositions in which the reaction product is used.

The acidic hydrogen-containing compound of (ii) may be a carboxylic acid or a phenolic compound. It is preferably a phenolic compound, more preferably a polyphenol. Suitable acidic hydrogen-containing compounds include benzoic acid, dodecanedioic acid, azelaic acid, itaconic acid, sebacic acid, and adipic acid. Suitable phenols include phenol itself and polyphenols such as resorcinol, catechol, hydroquinone, bis(4-hydroxyphenyl)- 2,2-propane (i.e., Bisphenol A), bis(4-hydroxyphenyl)-1,1-isobutane, bis(4-hydroxyphenyl)-1,1-ethane, bis(2-hydroxyphenyl)-methane, 4,4-dihydroxybenzophenone, and 1,5-dihydroxynaphthalene. Bisphenol A is preferred.

The oligomeric material of the present invention can be prepared by reacting the material of (i) with the acidic hydrogen-containing compound of (ii) in an equivalent ratio of about 1:1 to 1:2, preferably about 1:1.87. The material of (i) is typically heated to a temperature of about 140° to 180° C. and the acidic hydrogen-containing compound of (ii) is added. The reaction mixture is then usually held at the elevated temperature until it turns clear, indicating homogeneity of the reaction mixture. The reaction mixture is then allowed to cool.

The compositions of the present invention may be used as catalysts in curable compositions, particularly curable compositions comprising polyepoxides and crosslinking agents for the polyepoxides. The amount of catalyst is sufficient to effect cure of the curable composition; typically the catalyst is present in an amount ranging from about 0.5 to about 10 percent by weight, preferably from about 0.5 to about 4 percent by weight, based upon total weight of the curable composition.

The polyepoxides which are used in the curable compositions are preferably those which are suitable for use in induction curable adhesive compositions and which contain at least two 1,2-epoxide groups per molecule. In general, the epoxy equivalent weight can range from about 120 to about 760 based on solids of the polyepoxide. The polyepoxides may be saturated or unsaturated, may be aliphatic, alicyclic, aromatic, or heterocyclic. They may contain substituents such as halogens, hydroxyl groups, and ether groups.

Suitable classes of polyepoxides include epoxy ethers obtained by reacting an epihalohydrin such as epichlorohydrin with a polyphenol in the presence of an alkali. Suitable polyphenols include resorcinol, catechol, hydroquinone, bis(4-hydroxyphenyl)-2,2-propane (i.e., Bisphenol A), bis(4-hydroxyphenyl)-1,1-isobutane, bis(4-hydroxyphenyl)-1,1-ethane, bis(2-hydroxyphenyl)-methane, 4,4-dihydroxybenzophenone, and 1,5-dihydroxynaphthalene. The diglycidyl ether of Bisphenol A is preferred.

Other suitable polyepoxides include polyglycidyl ethers of polyhydric alcohols. These compounds may be derived from polyhydric alcohols such as ethylene glycol, propylene glycol, butylene glycol, 1,6-hexylene glycol, neopentyl glycol, diethylene glycol, glycerol, trimethylol propane, and pentaerythritol. These compounds may also be derived from polymeric polyols such as polypropylene glycol.

Examples of other suitable polyepoxides include polyglycidyl esters of polycarboxylic acids. These compounds may be formed by reacting epichlorohydrin or another epoxy material with an aliphatic or aromatic polycarboxylic acid such as succinic acid, adipic acid, azelaic acid, sebacic acid, maleic acid, 2,6-naphthalene dicarboxylic acid, fumaric acid, phthalic acid, tetrahydrophthalic acid, hexahydrophthalic acid, or trimellitic acid. Dimerized unsaturated fatty acids containing about 36 carbon atoms (Dimer Acid) and polymeric polycarboxylic acids such as carboxyl terminated acrylonitrile-butadiene rubber may also be used in the formation of these polyglycidyl esters of polycarboxylic acids.

Polyepoxides derived from the epoxidation of an olefinically unsaturated alicyclic compound are also suitable for use in the curable composition of the present invention. These polyepoxides are nonphenolic and are obtained by epoxidation of alicyclic olefins with, for example, oxygen, perbenzoic acid, acid-aldehyde monoperacetate, or peracetic acid. Such polyepoxides include the epoxy alicyclic ethers and esters well known in the art.

Other suitable polyepoxides include epoxy novolac resins. These resins are obtained by reacting an epihalohydrin with the condensation product of aldehyde and monohydric or polyhydric phenols. A typical example is the reaction product of epichlorohydrin with a phenol-formaldehyde condensate.

The polyepoxides can be partially defunctionalized by carboxylic acids, alcohol, water, phenols, mercaptans, or other monofunctional active hydrogen-containing compounds.

The curable composition of the present invention may contain one polyepoxide or preferably mixtures of polyepoxides. Mixtures are generally used in induction curable adhesive compositions.

Typically, the polyepoxide is present in the curable composition of the present invention in a range of from about 30 to about 90 percent, preferably from about 30 to 60 percent, based upon total weight of the curable composition.

Examples of crosslinking agents in the curable composition are latent crosslinking agents such as boron trifluoride monoethylamine complex, boron trifluoride diethylamine complex, boron trifluoride triethylamine complex, boron trifluoride pyridine complex, boron trifluoride benzyldimethylamine complex, boron trifluoride benzylamine, boron trifluoride etherate, and dicyandiamide. By latent is meant that these materials are inactive until the application of heat. Dicyandiamide is preferred.

The crosslinking agent is typically present in an amount ranging from about 3 to about 15 percent by weight, preferably from about 3 to about 10 percent by weight, based upon weight of the polyepoxide.

The curable compositions preferably contain an accelerator to initiate cure at a lower temperature. Examples of accelerators are bis-dimethyltolyl urea and dicumyl peroxide, which is preferred. When used, the accelerator is present in an amount ranging from about 2 to 8 percent by weight, based on total weight of the curable composition.

The curable compositions of the present invention may also contain a variety of additives including pigments such as carbon black, fillers such as calcium oxide and wollastonite, and thixotropes such as bentonite clay in amounts conventionally used in induction curable compositions.

The curable composition of the present invention may be applied to a substrate in a number of ways including spraying, extrusion, or by hand with a blade. Extrusion is the preferred method of application.

The composition may be cured by heating to a temperature of about 120° C. to about 200° C. for a period ranging from about 4 seconds to 30 minutes. Preferably the composition is cured by induction heating. In this process the curable composition is applied to a metal surface such as a flanged fixture associated with an automotive body panel. An induction coil operating with an electrical frequency of about 5 to about 30 megahertz, from an electromagnetic field generated by a power source of about 1 to about 30 kilowatts, more typically from about 5 to about 25 kilowatts, is positioned in close proximity to the coated surface so as to raise the temperature of the metal surface to a level sufficient to initiate cure of the composition, typically to a range of about 150° C. to about 180° C. The induction coil is maintained in position for a time sufficient to complete cure of the composition, typically for about 4 to 45 seconds, preferably for about 4 to about 11 seconds.

The invention will further be described by reference to the following examples. Unless otherwise indicated, all parts are by weight.

EXAMPLE A

The following ingredients were used to prepare an oligomeric material:

| Ingredient | Weight, g | Equivalents | Percent by weight |
| --- | --- | --- | --- |
| Dimethylaminopropylamine | 204.4 | 1.000 | 23.95% |
| Isophorone diisocyanate (IPDI)[1] | 222.2 | 1.000 | 26.05% |
| Bisphenol A[2] | 426.6 | 3.74 | 50.00% |

[1]Available from Hüls America, Inc.
[2]4,4'-Isopropylidenediphenol, available from Dow Chemical Co.

The dimethylaminopropylamine was charged to a suitable reactor and heated to 50° C. The IPDI was added through an addition funnel over a period of two hours. The temperature of the reaction mixture was allowed to increase to 90° C. during the addition. After the addition was complete the reaction mixture was heated to 130° C. and held at that temperature until infrared analysis indicated consumption of the isocyanate. The reaction mixture was then heated to 160° C. and the Bisphenol A was added. The reaction mixture was held at 160° C. until the solution turned clear, indicating complete melting of the Bisphenol A. The reaction mixture was poured out hot and allowed to cool and solidify. The final solid product had a solids content of about 98 percent and a number average molecular weight of 336 as measured by gel permeation chromatography using polystyrene as a standard.

EXAMPLES B–F

Solid oligomeric materials were made in manners similar to Example A, and their composition, solids content, and number average molecular weight (Mn) are reported in Table I below.

TABLE I

| Ingredient | B | C (Comparative) | D | E (Comparative) | F |
|---|---|---|---|---|---|
| IPDI | 204.4 | — | 55.6 | 111.1 | 111.1 |
| DMAPA[1] | 222.2 | 102.2 | — | — | 102.2 |
| BPA[2] | — | 189.3 | — | 241.3 | — |
| TDI[3] | — | 87.1 | — | — | — |
| DEAPA[4] | — | — | 65.1 | 130.2 | — |
| BA[5] | — | — | — | — | 213.3 |
| % solids | 100.0% | 100.0% | 100.0% | 98.8% | 90.7% |
| Mn | 560 | — | — | — | — |

[1]Dimethylaminopropylamine, available from Texaco chemicals.
[2]Bisphenol A
[3]Mondur TD-80: Toluene diisocyanate, available from Miles Inc.
[4]Diethylaminopropylamine, available from Aldrich Chemical Co.
[5]Benzoic acid, available from DSM Chemical Co.

EXAMPLES 1–8

Induction curable adhesive compositions were prepared from the following mixture of ingredients:

| Ingredient: | Parts |
|---|---|
| Epoxy-CTBN adduct[1] | 97 |
| Epoxy-dimer acid adduct[2] | 136 |
| EPON 828[3] | 285 |
| DER 736 epoxy[4] | 93 |
| Aluminum powder[5] | 155 |
| Vansil W-10[6] | 129.3 |
| Carbon black | 0.7 |
| Dicyandiamide | 34 |
| Cabosil TS-720[7] | 40 |
| Aerosil R 202[8] | 10 |
| Catalyst[9] | 2% |

[1]Adduct of carboxy terminated polyacrylonitrilebutadiene with EPON 828 at a mole ratio of 1:5, available from PPG Industries, Inc.
[2]Adduct of Dimer Fatty acid and EPON 828 in a 1 to 5 mole ratio, available from PPG Industries, Inc.
[3]Polyglycidyl ether of Bisphenol A, available from Shell Oil and Chemical Co.
[4]Polypropylene glycol diglycidyl ether available from Dow Chemical Co.
[5]Available from Reynolds Metals Co.
[6]Wollastonite clay available from R. T. Vanderbilt Co., Inc.
[7]Hydrophobic fumed silica, available from Cabot Corporation

| Ingredient: | Parts |
|---|---|

[8]Fumed silica, available from Degussa Corporation
[9]The solid oligomeric materials of Examples A to F, added as follows;
Example 1 contained the material of Example A
Example 2 contained the material of Example B
Example 3 contained the material of Example C
Example 4 contained the material of Example D
Example 5 contained the material of Example E
Example 6 contained the material of Example F Example 7 (comparative) contained dichlorodiphenyl bis-dimethyl urea catalyst, available from E. I. Du Pont de Nemours and Co. as Diuron, and Example 8 served as a control, containing no catalyst.

Properties of the various adhesive compositions are reported in Table II below.

TABLE II

| Example | Viscosity[1] | Reactivity[2] | Stability[3] |
|---|---|---|---|
| Example 1 | 147,843 | 29 | no gel |
| Example 2 (comparative) | 276,812 | 21 | gel[4] |
| Example 3 | 267,376 | 30 | no gel |
| Example 4 (comparative) | 243,784 | 30 | gel |
| Example 5 | 128,969 | 46 | no gel |
| Example 6 | 179,299 | 162 | no gel |
| Example 7 (comparative) | 106,950 | 57 | gel |
| Example 8 (control) | 133,688 | >240 | no gel |

[1]Measured at 78° F. (25.6° C.), measured at 0.5 rpm with a Brookfield cone and plate viscometer, expressed in centipoise
[2]Number of seconds to cure at 325° F. (162.8° C.)
[3]Samples were stored at 130° F. (54.4° C.) for three days unless otherwise noted
[4]Gelled within one day

We claim:

1. A composition comprising the reaction product of:

(i) a material having the structure:

$$[R_4-N(R_3)-R_2-N(H)-C(=O)-N(H)\frac{}{}]_n R_1$$

wherein $R_1$ is an organic radical having 6 to 25 carbon atoms, $R_2$ is alkylene having one to four carbon atoms; $R_3$ and $R_4$ are independently alkyl having one to four carbon atoms; and n is 2–4; and (ii) an acidic hydrogen-containing compound that provides a tertiary amino urea reaction product with a melting point to prevent melting before heating.

2. The composition of claim 1 wherein $R_1$ is 1,1,3,3-tetramethylcyclohexyl.

3. The composition of claim 1 wherein $R_2$ is n-propylene.

4. The composition of claim 1 wherein $R_3$ and $R_4$ are methyl.

5. The composition of claim 1 wherein (ii) is selected from the group consisting of a carboxylic acid and a phenolic compound.

6. The composition of claim 5 wherein the phenolic compound is a polyphenol.

7. The composition of claim 6 wherein the polyphenol is bis(4-hydroxyphenyl)-2,2-propane.

8. The composition of claim 1 wherein the equivalent ratio of (i) to (ii) is about 1:1 to 1:2.

9. A curable composition comprising:

(a) a polyepoxide;

(b) a crosslinking agent;

(c) an accelerator; and (d) a composition comprising the reaction product of:

(i) a material having the structure:

$$[R_4-N-R_2-N-C-N\frac{}{n}R_1]$$
with $R_3$ on first N, H on middle N, H on C-N, and =O on C wherein $R_1$ is an organic radical having 6 to 25 carbon atoms, $R_2$ is alkylene having one to four carbon atoms; $R_3$ and $R_4$ are independently alkyl having one to four carbon atoms; and n is 2–4; and (ii) an acidic hydrogen-containing compound.

10. The curable composition of claim 9 wherein (a) is present in an amount ranging from about 30 to about 90 percent by weight, based upon total weight of the curable composition.

11. The curable composition of claim 9 wherein the crosslinking agent of (b) is present in an amount ranging from about 3 to about 15 percent by weight, based upon weight of (a).

12. The curable composition of claim 11 wherein the crosslinking agent of (b) is dicyandiamide.

13. The curable composition of claim 9 wherein the accelerator of (c) is present in an amount ranging from about 2 to about 8 percent by weight, based upon total weight of the curable composition.

14. The curable composition of claim 13 wherein the accelerator of (c) is a peroxide.

15. The curable composition of claim 14 wherein the accelerator of (c) is dicumyl peroxide.

16. The curable composition of claim 9 wherein (d) is present in an amount ranging from about 0.5 to about 10 percent by weight, based upon total weight of the curable composition.

17. The curable composition of claim 9 wherein the acidic hydrogen-containing compound is a phenolic compound.

18. The curable composition of claim 17 wherein the phenolic compound is a polyphenol.

19. The curable composition of claim 18 wherein the polyphenol is bis(4-hydroxyphenyl)-2,2-propane.

20. A process of curing a curable composition comprising:

1) applying a curable composition to a metal surface wherein the curable composition comprises:
   (a) a polyepoxide;
   (b) a crosslinking agent;
   (c) an accelerator; and
   (d) a composition comprising the reaction product of:

(i) a material having the structure:

$$[R_4-N-R_2-N-C-N\frac{}{n}R_1]$$
with $R_3$ on first N, H on middle N, H on C-N, and =O on C wherein $R_1$ is an organic radical having 6 to 25 carbon atoms, $R_2$ is alkylene having one to four carbon atoms; $R_3$ and $R_4$ are independently alkyl having one to four carbon atoms; and n is 2–4; and (ii) an acidic hydrogen-containing compound;

2) positioning an induction coil operating at a high electrical frequency into close proximity to the coated metal surface to raise the temperature of the coated metal surface to a level sufficient to initiate cure of the composition;

3) maintaining the induction coil in position for a time sufficient to complete cure of the composition.

21. The process of claim 20 wherein (a) is present in an amount ranging from about 30 to about 90 percent by weight, based upon total weight of the curable composition.

22. The process of claim 20 wherein the crosslinking agent of (b) is present in an amount ranging from about 3 to about 15 percent by weight, based upon weight of (a).

23. The process of claim 20 wherein the crosslinking agent of (b) is dicyandiamide.

24. The process of claim 20 wherein the accelerator of (c) is present in an amount ranging from about 2 to about 8 percent by weight, based upon total weight of the curable composition.

25. The process of claim 20 wherein the accelerator of (c) is a peroxide.

26. The process of claim 25 wherein the accelerator of (c) is dicumyl peroxide.

27. The process of claim 18 wherein (d) is present in an amount ranging from about 0.5 to about 10 percent by weight, based upon total weight of the curable composition.

28. The process of claim 20 wherein the acidic hydrogen-containing compound is a phenolic compound.

29. The process of claim 28 wherein the phenolic compound is a polyphenol.

30. The process of claim 29 wherein the polyphenol is bis(4-hydroxyphenyl)-2,2-propane.

31. The process of claim 20 wherein the curable composition is applied by extrusion.

32. The process of claim 20 wherein the electrical frequency is from about 5 to about 30 megahertz.

33. The process of claim 20 wherein the temperature is from about 150° C. to about 180° C.

34. The process of claim 20 wherein the time is from about 4 to about 45 seconds.

35. The composition of claim 1 wherein (ii) is a solid material.

36. The composition of claim 35 wherein (ii) is crystalline.

* * * * *